United States Patent
Schram et al.

(10) Patent No.: US 6,761,056 B2
(45) Date of Patent: Jul. 13, 2004

(54) PROCESS AND DEVICE FOR PRODUCING A GAS MIXTURE WHICH CONTAINS AT LEAST ONE GASEOUS COMPONENT, IN PARTICULAR FOR PRODUCING A CALIBRATION GAS

(75) Inventors: Jurgen Schram, Krefeld (DE); Thomas Albinus, Krefeld (DE)

(73) Assignee: Gerstel Systemtechnik GmbH & Co., Mulheim (DE)

( * ) Notice: Subject to any disclaimer, the term of this patent is extended or adjusted under 35 U.S.C. 154(b) by 141 days.

(21) Appl. No.: 10/106,610
(22) Filed: Mar. 26, 2002
(65) Prior Publication Data
US 2002/0139167 A1 Oct. 3, 2002

(30) Foreign Application Priority Data
Mar. 27, 2001 (DE) .......................... 101 14 947

(51) Int. Cl.[7] ............................................. G01N 21/00
(52) U.S. Cl. ........................................................ 73/1.05
(58) Field of Search ............................. 73/1.02–1.05, 73/863.11, 865.5, 861.81, 61.59; 261/78.1, 115

(56) References Cited

U.S. PATENT DOCUMENTS

| 3,889,538 | A | * | 6/1975 | Fingerle ................. 73/863.11 |
| 4,162,897 | A | * | 7/1979 | Capuano ..................... 436/106 |
| 4,405,344 | A | | 9/1983 | Sisti et al. |
| 4,667,877 | A | | 5/1987 | Yao et al. |
| 4,793,173 | A | * | 12/1988 | Moreth et al. ................ 73/1.03 |
| 5,145,113 | A | | 9/1992 | Burwell et al. |
| 5,152,457 | A | | 10/1992 | Burwell et al. |
| 5,305,630 | A | * | 4/1994 | Molozay et al. .............. 73/1.05 |
| 5,400,665 | A | | 3/1995 | Zhu et al. ................. 73/863.12 |
| 5,540,251 | A | | 7/1996 | Mayeaux ....................... 137/88 |
| 5,587,519 | A | * | 12/1996 | Ronge et al. ................. 73/1.05 |
| 5,766,682 | A | | 6/1998 | Tsubouchi et al. |
| 6,102,512 | A | * | 8/2000 | Torii et al. .................... 347/10 |

FOREIGN PATENT DOCUMENTS

| DE | 2151007 | 4/1973 |
| DE | 3819100 | 12/1989 |
| DE | 19626428 | 1/1998 |
| DE | 19858366 | 6/2000 |
| DE | 19938239 | 3/2001 |
| GB | 1 449 929 | 9/1976 |
| GB | 2284364 A | 6/1995 |
| JP | 60027412 | 8/1986 |

* cited by examiner

Primary Examiner—Robert Raevis
(74) Attorney, Agent, or Firm—Patterson, Thuente, Skaar & Christensen, P.A.

(57) ABSTRACT

The invention relates to a process and a device for producing a gas mixture which contains at least one gaseous trace component, in particular for producing a calibration gas, in which a matrix gas stream is conveyed continuously with a predetermined quantitative flow, and at least one calibration component is introduced into the matrix gas stream in a predetermined quantity per unit volume of matrix gas, the at least one calibration component being introduced in the form of microdroplets of substantially identical size and being evaporated in the matrix gas to form the calibrating gas mixture, the microdroplets being delivered by nozzles which are in each case made to contract by means of a piezoelement which is triggered by metering pulses which are generated according to the intended delivery quantity.

30 Claims, 3 Drawing Sheets

PROCESS AND DEVICE FOR PRODUCING A GAS MIXTURE WHICH CONTAINS AT LEAST ONE GASEOUS COMPONENT, IN PARTICULAR FOR PRODUCING A CALIBRATION GAS

FIELD OF THE INVENTION

The invention relates to a process and a device for producing a gas mixture which contains at least one gaseous component, in particular for producing a calibration gas.

The use of gases with defined concentrations of admixtures is required both in various technical devices and as calibration standards for analysis methods.

BACKGROUND OF THE INVENTION

In all analytical devices, calibration represents the most important step with a view to obtaining correct results from the analysis. Although the apparatus settings of an analysis device may have a decisive influence on the sensitivity and accuracy of an analysis result (and therefore the detection limit), correctness can only be ensured by comparison with a calibration specimen with a known content.

In the environmental analysis field, the need for global, time-independent comparability of analysis results, means that correctness is a crucial parameter if it is to be possible to understand ecological processes and understand global mass streams. Nowadays, the analysis of gaseous pollutants down to the lower ppt range no longer constitutes any problem for many analysis devices, for example those used in gas chromatography. However, the problem of appropriate calibration of such analyses remains substantially unresolved.

A continuous stream of the calibration gas is required in order to filter out any conditioning phenomena. The requirements of trace analysis of gaseous pollutants make continuously flowing certified test gases from pressurized-gas vessels the optimum calibration medium. The high price, caused by complex stabilization and production, and the long delivery times, which are caused by production factors, and also the high minimum volumes of the individual vessels make these processes appear too expensive for many users. Moreover, not all gas mixtures can be stabilized in corresponding pressure systems, with the metal surfaces which they employ. In particular, polar components can only be produced in stabilized form with very great difficulty by this route.

An ideal calibration specimen generally contains an accurately defined concentration of the analyte, distributed as homogeneously as possible in the same matrix gas which also surrounds the analysis specimen. However, a calibration specimen of this type can rarely be achieved, in particular in the field of environmental analysis, since it is almost impossible to obtain the uncontaminated matrix required for production of the calibration specimen as a blank and dilution medium.

There is another problem with regard to the analysis of gaseous specimens. Although in this case it is relatively easy to obtain the uncontaminated matrix, for example synthetic air, in this case the production of corresponding standard specimens represents a problem.

Gravimetric methods of producing gas mixtures are extremely complex and can only be undertaken by manufacturers of test gases with considerable financial outlay. This results in problems on account of the masses of the vessels which hold the gas mixture, which are high in relation to the matrix gases, but very particularly in relation to the trace components.

In the case of volumetric production, it must be possible for small volumes of a trace component, which is often in liquid form, to be introduced reproducibly into a very large volume of the matrix gas. There are problems with the stability of the gas mixtures on account of the low density of the gaseous analyte. Adsorption and desorption on the surfaces of the equipment which is in contact with the test gas, which surfaces are very large in relation to the mass of the trace components, lead to the risk of the concentration changing, for example on account of wall desorption and wall adsorption effects.

Commercially available calibration systems which attempt to achieve this have various weak points:
 a short operating range of at most two decades,
 problems with low concentrations,
 limits on the number of components which can be mixed and their ratios,
the minimum achievable concentration range is excessively high.

It is also known for the pure components to be introduced continuously into a continuously flowing gas stream and to be reproducibly homogenized therewith. In this case, critical nozzles, permeation devices or controlled incoming flows of test gases of higher concentrations may be suitable for introduction. However, this does not solve the above problems.

Since, by definition, the detection limit of all analytical devices is decisively dependent on the reproducibility of the individual results, any improvement in the calibration also improves the detection limit and therefore considerably increases the capacity of the overall analysis device.

DE 198 58 366 A1 has disclosed a process of the type described in the introduction in which a capillary diffusion metering system is used in order to establish a defined mixing ratio of a carrier gas and the components which are of interest. Then, the mixture is passed over a trap, through which a purge-gas stream is passed, the components which are of interest being transferred into this stream. However, the accuracy which can be achieved is by no means sufficient for some applications.

U.S. Pat. No. 5,400,665 discloses a process for producing an analysis gas stream in which a liquid mist comprising small drops of a sample which is to be analysed is produced, solvent being eliminated, before the mist is introduced into a carrier gas stream, by heating the mist. In this case, the mist droplets are produced by means of a piezoelement. Apart from the fact that the mist does not contain substantially uniform droplets, but rather, at a frequency of 1.3 MHz, 70% of the droplets are smaller than 13 $\mu$m, with the larger droplets being separated out under the force of gravity, this process is not suitable for the production of a gas mixture which contains at least one gaseous trace component in a predetermined concentration, especially since there is no quantitative metering of the sample material.

SUMMARY OF THE INVENTION

It is an object of the invention to provide a process which makes it possible to prepare a gas mixture with a known concentration of volatile components on-line even. It is a further object of the invention to provide a process which allows to prepare a gas mixture with a very low concentration range of volatile components. It is still a further object of the invention to provide a process for preparing a gas mixture usuable as calibration standard or for industrial processes.

It is also an object of the invention to provide a device which makes it possible to prepare a gas mixture with a known concentration of volatile components on-line even and especially one having with a very low concentration range of volatile components.

The invention concerns a process for producing a gas mixture which contains at least one gaseous trace component in a predetermined concentration, comprising the steps of:

continuously conveying a matrix gas stream with a predetermined quantitative flow;

introducing at least one trace component into the matrix gas stream in a predetermined quantity per unit volume of matrix gas;

wherein the at least one trace component is introduced in the form of successive microdroplets of substantially the same size and is evaporated in the matrix gas to form the gas mixture, the microdroplets being delivered from at least one nozzle, which is in each case made to contract by means of a piezoelement which is triggered by metering pulses which are generated according to an intended delivery quantity per unit time.

The invention further comprises a device for producing a gas mixture which contains at least one gaseous trace component in a predetermined concentration, comprising a matrix gas source, downstream of which there is a mass flow controller, and at least one source for a component, and a metering device for the at least one trace component, wherein the metering device is a microdroplet-metering device with at least one nozzle which releases successive individual microdroplets, opens out into an evaporator tube, through which the matrix gas flows, and can be made to contract, so as to produce a microdroplet, by means of a piezoelement which is triggered by metering pulses generated according to the intended delivery quantity per unit time.

In this arrangement, a matrix gas stream is conveyed continuously, with a predetermined quantitative flow, and at least one calibration component is introduced into the matrix gas stream in a predetermined quantity per unit volume of matrix gas, the at least one calibration component being introduced in the form of microdroplets of substantially identical size and being evaporated in the matrix gas to form the calibration gas or mother mixture, the microdroplets being delivered by nozzles which are in each case made to contract by means of a piezoelement which is triggered by trigger pulses which are generated according to the intended delivery quantity. This results in a continuous calibration-gas stream with a known concentration of volatile, in particular highly volatile components, in particular under standard pressure. It is possible for dilute gas mixtures comprising a very wide range of components in a very wide range of concentration ratios to be produced on line and made available to the sample introduction system for a gas analysis device which is to be calibrated. If appropriate, the calibration component can be cooled in order to be in the liquid state so that it can be introduced as microdroplets.

Either a solution which contains the components, with one metering head, or a plurality of metering heads amounting to the same number as the number of components, can be used to produce multicomponent gas mixtures.

In this way, it is possible to ensure a highly accurately controlled introduction of a sample into a continuous gas stream and, thereby, to offer ideal conditions for a flexible calibration system. The quantities of analyte substance which are required for calibration are introduced into a carrier gas stream (in particular $N_2$ or synthetic air) which is controlled by an accurate mass flow controller from one microdroplet-delivery device or preferably from a plurality of microdroplet-delivery devices which in each case supply different components. Separate actuation of each microdroplet-delivery device makes it possible to achieve a very wide range of mixing ratios for the component in the gas phase. Moreover, on account of the small droplet size which is to be achieved (in the range from, for example, approximately 20 to 100 $\mu$m, in particular approximately 30 to 50 $\mu$m), rapid and complete evaporation of the components in the carrier gas stream is ensured. This leads to a homogeneous calibration or test gas. The possibility of introducing 1 to 2000 drops/sec of a volume of approximately 15 to 65 pl of each component into a given gas stream alone allows calibration over more than four concentration decades without the device having to be mechanically altered. Therefore, a process of this type has a considerably greater flexibility with regard to concentration range and component ratios than the processes or test gases which have hitherto been commercially available.

In this way, the accuracy of the analysis results on defined standard samples and also of real samples can be increased considerably, at low cost, compared to conventional calibration techniques, and therefore the reproducibility and, as a result, the detection limit can also be lowered greatly. Furthermore, the calibration gas is available for rapid use, for example in the laboratory.

After the droplet size has been determined—by gravimetry or by determining the flow rate in a capillary section—the calibration generation can be set digitally and therefore in a readily automated manner—by digital setting of the drop frequency—to the desired test gas concentration. Moreover, during the sequence, this concentration can be digitally altered at any time, in order to generate an automatic calibration series of different test gas concentrations. A further advantage is that it is also possible to generate test gases of polar components, which cannot be obtained in commercially available pressurized-gas vessels.

The uniform size and sequence of the drops ensure that a homogeneous gas mixture is formed, as is optimum for calibration purposes. Digitally controlling the microdroplet-metering device allows from 1 to 2000 drops with a volume of 15 pl (with a nozzle diameter of d=30 $\mu$m) of each component to be introduced into a given gas stream. This allows calibration over more than four decades without the system having to be mechanically changed. To obtain an optimally calibrated gas mixture, the size and homogeneity of the individual drops formed are of crucial importance. If the droplets are of optimum size, the final liquid volume by which the total quantity of trace components is distributed in the matrix gas is dependent solely on the homogeneity of the size distribution. Production of the microdroplets is distinguished by an extremely reproducible method of operation, and the scatter of the individual drop sizes, based on the mass, is approximately 1%, i.e. well below the scatter of comparable processes. The fact that the calibration components are introduced into the matrix gas as microdroplets and not, for example, as a film of liquid leads to the evaporation process taking place highly reproducibly given the same size of droplet, so that a homogeneous gas mixture can be formed.

The precise volumetric flow of matrix gas required in the calibration unit can be ensured by mass flow controllers.

These control instruments are expediently used on the matrix gas side to allow ideal calibration thereof and to eliminate any possible disruptive influences from the trace components, which are often reactive and therefore corrosive.

The increases in volume which are to be expected from the evaporation of the trace components can be determined by calculation and taken into account when controlling the microdroplet-metering devices.

The process can be used universally for all analysis methods employed for highly volatile components (for example VOCs and VVOCs). These gas analysis methods are becoming increasingly important in the application areas of instrumental analysis, which are becoming increasingly important such as for example environmental analysis (climate protection) or analysis in the field of health and safety at work. Calibration gases which have been produced in accordance with the invention can be used in gas chromatography devices, gas phase adsorption and desorption devices, in infrared spectroscopy, in UV/VIS spectroscopy or in gas-phase monitoring devices.

As well as applications in chemical analysis, further fields include areas in which ideally defined gas phases can be used, such as climatic chambers, sensor test stands or vapour phase epitaxy systems. The process can also be used to provide, for example, certain gases, such as natural gas, or atmospheres, such as air, with a defined fragrance content.

The quantitative determination of the various gaseous pollutants in atmosphere and ambient air has considerable importance both for climate protection and for health and safety at work. Especially in an industrial society, the ecological effects of gaseous pollutants are of considerable importance, on account of their high diffusion rates and the wide-ranging ways in which they can be conveyed in the environmental compartment air for introduction into the ecosphere. Therefore, contamination of the environmental compartment air by a very wide range of gaseous pollutants play an important role particularly with regard to direct damage, but also to increased levels in ecosystems. In this context, correct analysis results in particular of individual trace components are of particular interest, since these components often have highly damaging effects on ecosystems on account of their ecotoxicological action. The harmful action of highly volatile hydrocarbons (VVOCs and VOCs) are only one example. Accuracy of analysis of these substances, which can often accumulate in ecosystems on account of persistence, has to be constantly improved. Only in this way can all introduction paths, including the natural, low-concentration paths be recorded correctly on a global basis even over prolonged periods of time.

Further objects, embodiments and advantages of the invention are to be found in the following description.

BRIEF DESCRIPTION OF THE DRAWINGS

The invention is explained in more detail below with reference to the appended drawings, in which.

DETAILED DESCRIPTION OF A PREFERRED EMBODIMENT

Figure 1:
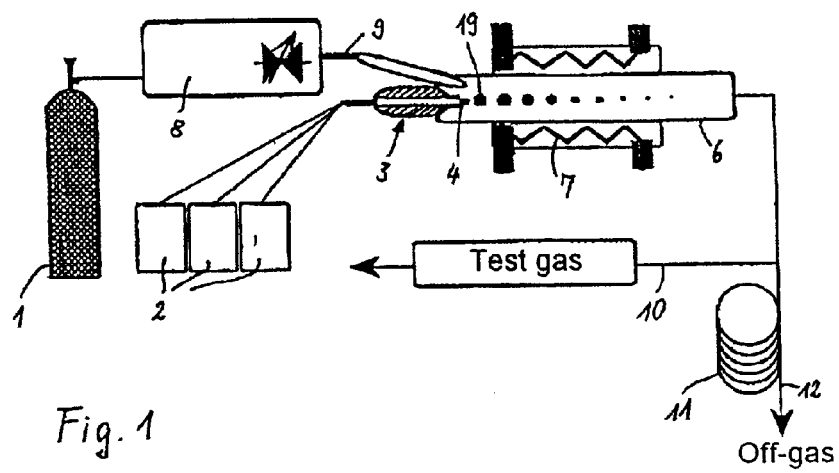
FIG. 1 diagrammatically depicts an embodiment of a device for generating a calibration gas.
Figure 2:
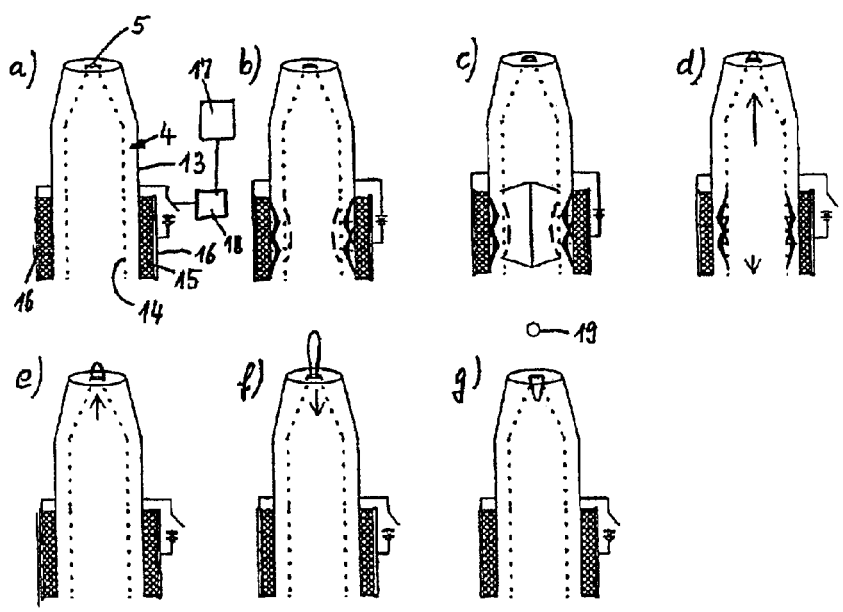
FIG. 2 diagrammatically depicts the formation of microdroplets by a nozzle of a microdroplet-metering device.

As shown in FIG. 1, a matrix gas source 1, for example a gas cylinder containing an ultra pure gas, and sources 2 for various calibration components, which are in liquid form, are provided. The latter are connected to a microdroplet-metering device 3, which comprises a corresponding number of nozzles 4, the outlet openings 5 (cf. FIG. 2) of which are directed into the interior of an evaporator tube 6. The evaporator tube 6 is surrounded by a heater device 7, for example a heating coil comprising a resistor wire, and is connected on the inlet side, i.e. adjacent to the microdroplet-metering device 3, to a line 9 which is controlled by a mass flow controller 8. The evaporator tube 6 can be heated to a predetermined temperature in a controlled manner by the heater device 7. On the outlet side, the evaporator tube 6 is connected to a discharge line 10 for calibration gas. Moreover, an off-gas line 12, which has a capillary 11 used to protect against back-diffusion, for excessive calibration gas branches off from the discharge line 10.

As is diagrammatically illustrated in FIG. 2a, each nozzle 4 comprises a nozzle body 13 having an inner bore 14 which is connected to the associated source 2 and leads to a narrowed outlet opening 5. The nozzle body 13 is surrounded by a piezoelement 15, whose electrodes 16 located on the outer side are connected to a metering pulse transmitter 18 which can be triggered by an in particular digital control unit 17. The application of a voltage pulse as metering pulse causes the piezoelement 15 to deform and therefore also causes the wall of the nozzle body 13 to be deformed, in this case contracted, cf. FIG. 2b. As a result, a pressure wave runs in both directions of the longitudinal axis of the nozzle 4, cf. FIG. 2c. As a result, the liquid in the inner bore 14 is correspondingly accelerated, and a defined quantity of liquid emerges from the outlet opening 5. A pressure drop takes place at the end of the voltage pulse, since the contraction is relieved. A reduced-pressure wave runs in both directions, FIG. 2d. The reduced-pressure wave reaches the outlet opening 5, the liquid is decelerated, FIG. 2e. The liquid vibrates back and a microdroplet 19 is constricted, FIG. 2f. The liquid column vibrates back inwards, FIG. 2g.

The pulsed contraction of the nozzle body 13 leads to a corresponding pulsed delivery of microdroplets 19, which form a finely divided aerosol and, on account of their small size and large surface area, evaporate completely in the evaporator tube 6.

Figure 3:
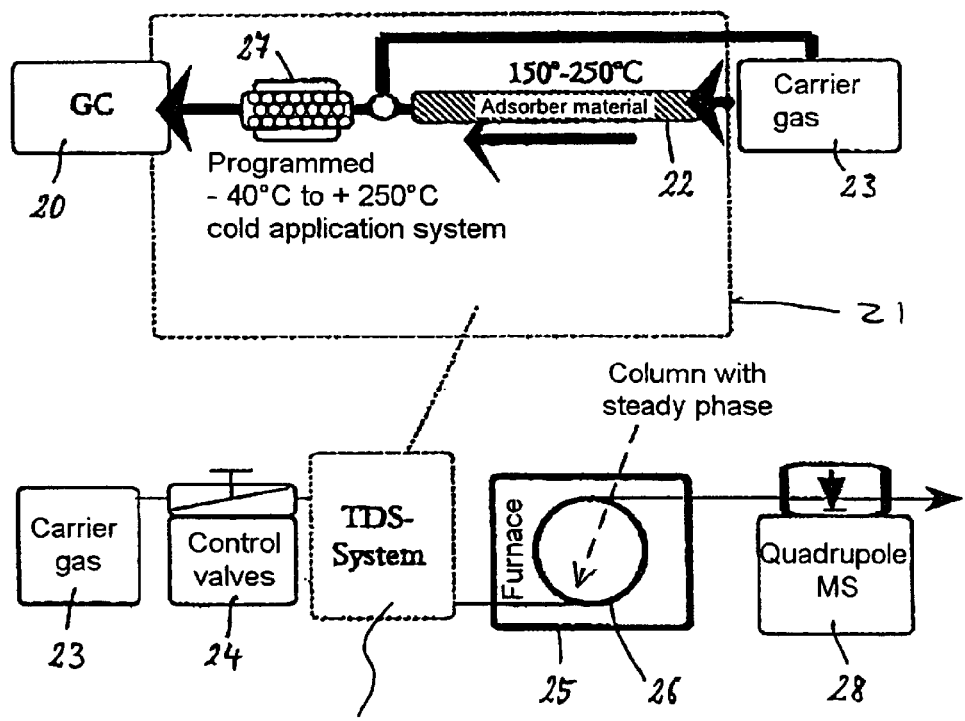
FIG. 3 diagrammatically depicts a thermal desorption device for introducing samples for a gas chromatograph.

A thermal desorption device 21 has proven to be a sampling/sample introduction system (TDS) which can be successfully coupled to a gas chromatograph 20. In this case, as illustrated in FIG. 3, for sampling purposes a large gas volume of a few liters to a few m$^3$ is sucked through a small tube 22 filled with an adsorption medium and, in the process, the trace components are adsorbed on the filling (e.g. silica gel or Tenax), so that the levels of trace components increase at that location. For analysis, the small tube 22 is then heated in a programmed manner, with a carrier gas, which originates from a carrier-gas source 23, flowing through it in a manner which is controlled by control valves 24, this gas introducing the trace components, which are desorbed under these conditions, into the gas chromatograph 20. This introduction may take place either directly onto a separation column arranged in a furnace 25 or initially, in order to increase the levels, into a cold trap 27 (e.g. cold application system) which can likewise be heated programmably. The problem of calibration arises in particular with this type of sample introduction. This is because it cannot be assumed that the degree of adsorption and therefore the recovery rate is 100%, in particular for trace components. For this reason it is necessary, contrary to current practice, for the system to be calibrated with a continuous test-gas stream. The separation column 26 is in this case connected to an analysis unit 28, for example a quadrupole mass spectrometer.

Figure 4:
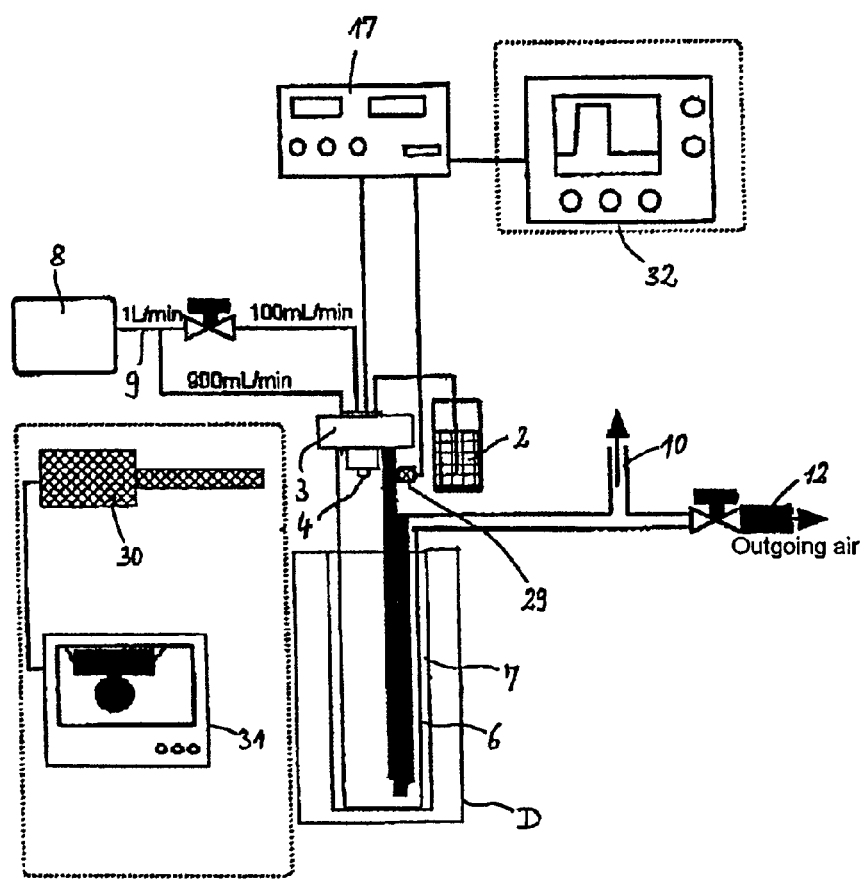
FIG. 4 diagrammatically depicts a further microdroplet-metering device for a thermal desorption device of a gas chromatograph.

As illustrated in FIG. 4, the embodiment of the microdroplet-metering device 3 illustrated in that figure may be supplied with matrix gas, for example ultrapure gas such as nitrogen, via the mass flow controller 8 in a controlled manner in order for calibrating gas to be generated in two different mass streams, in this case of 900 ml/min and, via an open valve, 100 ml/min. Under ultra pure gas conditions, the matrix gas stream can be mixed by the microdroplet-metering device 3 with one or more components from sources 2 which can be determined sensitively by gas chromatography. The small mass stream of 100 ml/min is used to flush around the nozzles 4 in order to carry the microdroplets 19 onward into the evaporator tube 6. The evaporator tube 6 in this case leads in a U shape to the discharge line 10 and is completely surrounded by the heater device 7. The evaporator tube 6 and the heater device 7 are arranged in a Dewar vessel in order to even out the distribution of heat in the evaporator tube 6.

In this case, visual control of the microdroplet formation is also provided, comprising a stroboscope diode 29 which is observed by means of a camera 30, which for its part is connected to a monitor 31, which can be used for visual monitoring of the metering. Moreover, an oscilloscope 32, which is used to control the metering pulse, is connected to the control unit 17. The discharge line 10 is in this case provided with a valve.

If, to produce multi-component gas mixtures, a solution which contains the components takes place with only one metering head and therefore only one nozzle, it can be admixed, for example, by using a methanolic solution with, for example, at most 1% by weight of foreign matter, i.e. calibration components or analytes. This means that the parameters of the solution which are decisive for operation, i.e. its viscosity and wetting behaviour, remain constant, since they are primarily dependent on the methanol. Therefore, given constant apparatus parameters, it is possible to produce a very wide range of gas mixtures. However, in this case the solvent, for example methanol, is also always present in the gas. However, this solvent content is very low compared to known processes which involve solutions being metered in.

The mechanical components of the device are independent of the mixture which is to be produced, and a change in the concentration of the mixture is achieved only by changing a parameter which can be set digitally, namely the frequency of drop delivery, i.e. without changing volumetric flows of gases. This can be reproduced with a very high level of accuracy and is correspondingly reliable.

While the invention has been shown and described with reference to the preferred embodiment, it should be apparent to one ordinary skilled in the art that many changes and modifications may be made without departing from the spirit and scope of the invention as defined in the claims.

What is claimed is:

1. A process for producing a gas mixture which contains at least one gaseous trace component in a predetermined concentration, comprising the steps of:
    continuously conveying a matrix gas stream with a predetermined quantitative flow;
    introducing at least one trace component into the matrix gas stream in a predetermined quantity per unit volume of matrix gas;
    wherein the at least one trace component is introduced in the form of successive microdroplets of substantially the same size and is evaporated in the matrix gas to form the gas mixture, the microdroplets being delivered from at least one nozzle, which is in each case made to contract by means of a piezoelement which is triggered by metering pulses which are generated according to an intended delivery quantity per unit time.

2. The process according to claim 1, wherein the matrix gas stream which contains the microdroplets is heated.

3. The process according to claim 1, wherein the volumetric expansion effected by the evaporation and, if appropriate, by heating is taken into account during the control of the quantitative flow of the matrix gas stream.

4. The process according to claim 1, characterized in that the matrix gas used is an ultra pure gas.

5. The process according to claim 1, characterized in that microdroplets with a uniform diameter from the range from approximately 30 to 50 $\mu$m are introduced.

6. The process according to claim 1, characterized in that the microdroplets are carried away from the at least one nozzle by a gentle matrix gas part stream which flushes around the at least one nozzle.

7. The process according to claim 1, characterized in that the at least one trace component is introduced dropwise in the form of a solution containing the trace components in a predetermined concentration.

8. The process of claim 1, used for producing a calibration gas.

9. A device for producing a gas mixture which contains at least one gaseous trace component in a predetermined concentration, comprising a matrix gas source, downstream of which there is a mass flow controller, and at least one source for a component, and a metering device for the at least one trace component, wherein the metering device is a microdroplet-metering device with at least one nozzle which releases successive individual microdroplets, opens out into an evaporator tube, through which the matrix gas flows, and can be made to contract, so as to produce a microdroplet, by means of a piezoelement which is triggered by metering pulses generated according to the intended delivery quantity per unit time.

10. The device according to claim 9, wherein the evaporator tube is heatable.

11. The device according to claim 9, wherein in particular a digital control unit for controlling the length and sequence of the metering pulses is provided for the microdroplet-metering device.

12. The device according to claim 9, wherein a gentle matrix gas part-stream, which is directed into the evaporator tube, can flush around the nozzles.

13. A process for calibrating a gas analysis device by passing through the device, and analysing therein, a calibration gas the method comprising
    introducing a matrix gas stream into the device at a predetermined quantitative flow, and
    introducing at least one calibration component, before the matrix gas stream is passed through the device, into the matrix gas stream in a predetermined quantity per unit volume of matrix gas,
    wherein the at least one calibration component is in the form of microdroplets of substantially identical size and is evaporated in the matrix gas stream to form the calibration gas, the microdroplets being delivered by at least one nozzle, which is in each case made to contract by means of a piezoelement which is triggered by metering pulses which are generated according to the intended delivery quantity per unit time.

14. The process according to claim 13, wherein the matrix gas stream together with the microdroplets is heated.

15. The process according to claim 13, wherein the volumetric expansion which is effected by the evaporation and, if appropriate, by heating is taken into account during the controlling of the quantitative flow of the matrix gas stream.

16. The process according to claim 13, wherein the matrix gas used is an ultra pure.

17. The process according to claim 13, wherein microdroplets with a uniform diameter in the range from approximately 30 to 50 μm are introduced.

18. The process according to claim 13, wherein the microdroplets are carried away from the nozzles by a gentle matrix gas part stream which flushes around the nozzles.

19. The process according to claim 13, wherein one or more calibration components are introduced dropwise in the form of a solution containing these components in a predetermined concentration.

20. The process according to claim 1, wherein the concentration of the trace component(s) is changed by changing the frequency of the trigger pulses.

21. The process according to claim 2, characterized in that the matrix gas used is an ultra pure gas, in particular synthetic air or nitrogen.

22. The process according to claim 3, characterized in that the matrix gas used is an ultra pure gas, in particular synthetic air or nitrogen.

23. The process according to claim 2, characterized in that the microdroplets are carried away from the at least one nozzle by a gentle matrix gas part stream which flushes around the at least one nozzle.

24. The process according to claim 3, characterized in that the microdroplets are carried away from the at least one nozzle by a gentle matrix gas part stream which flushes around the at least one nozzle.

25. The process according to claim 4, characterized in that the microdroplets are carried away from the at least one nozzle by a gentle matrix gas part stream which flushes around the at least one nozzle.

26. The process according to claim 4, wherein the ultra pure gas comprises synthetic air or nitrogen.

27. The process according to claim 5, characterized in that the microdroplets are carried away from the at least one nozzle by a gentle matrix gas part stream which flushes around the at least one nozzle.

28. The process according to claim 13, wherein the concentration of the trace component(s) is changed by changing the frequency of the trigger pulses.

29. The process according to claim 13, wherein the device comprises a gas chromatograph.

30. The process according to claim 16, wherein the ultra pure gas comprises synthetic air or nitrogen.

* * * * *

UNITED STATES PATENT AND TRADEMARK OFFICE
CERTIFICATE OF CORRECTION

PATENT NO. : 6,761,056 B2
DATED : July 13, 2004
INVENTOR(S) : Jurgen Schram and Thomas Albinus It is certified that error appears in the above-identified patent and that said Letters Patent is hereby corrected as shown below:

Column 9,
Line 5, please insert the word -- gas -- after the word "pure".

Signed and Sealed this

First Day of March, 2005

JON W. DUDAS
*Director of the United States Patent and Trademark Office*